United States Patent [19]

LaFreniere et al.

[11] Patent Number: 5,088,335
[45] Date of Patent: Feb. 18, 1992

[54] PERIODICALLY ACTIVATED CONSTANT PRESSURE MAINTAINING PISTONED CHAMBER LIQUID SAMPLER

[75] Inventors: Bryant R. LaFreniere, Midland; Mark T. Zaranski, Freeland; Marvin P. Miller, Midland, all of Mich.

[73] Assignee: The Dow Chemical Company, Midland, Mich.

[21] Appl. No.: 485,045

[22] Filed: Feb. 26, 1990

Related U.S. Application Data

[63] Continuation-in-part of Ser. No. 316,274, Feb. 27, 1989, abandoned.

[51] Int. Cl.$^5$ .............................................. G01N 1/14
[52] U.S. Cl. ..................... 73/864.62; 73/863.86
[58] Field of Search ........... 73/863.81, 863.83, 863.84, 73/863.86, 864.62, 863.01, 863.02, 863.03

[56] References Cited

U.S. PATENT DOCUMENTS

| | | | |
|---|---|---|---|
| 3,789,670 | 2/1974 | Rosenwald | 73/864.62 |
| 3,793,888 | 2/1974 | Rosenwald | 73/864.62 |
| 4,037,475 | 7/1977 | Topham | 73/863.01 |
| 4,172,670 | 10/1979 | Welker | 73/864.62 X |
| 4,459,865 | 7/1984 | Welker | 73/864.62 |
| 4,463,599 | 8/1984 | Welker | 73/864.62 X |
| 4,527,436 | 7/1985 | Jones | 73/863.84 |
| 4,532,813 | 8/1985 | Rinehart | 73/863.02 |
| 4,794,085 | 12/1988 | Jessop et al. | 73/863.01 X |
| 4,835,109 | 5/1989 | Trisciani et al. | 73/61.1 C |

Primary Examiner—Tom Noland

[57] ABSTRACT

A plurality of liquid samples are introduced successively to and stored in a variable volume chamber formed in a sample container by periodically establishing communication between the chamber and a liquid source and increasing the volume of the chamber by the exact amount of the sample that is introduced into the chamber, and without varying the pressure of the liquid entering or accommodated in the chamber. The chamber remains at all times completely filled with liquid.

27 Claims, 1 Drawing Sheet

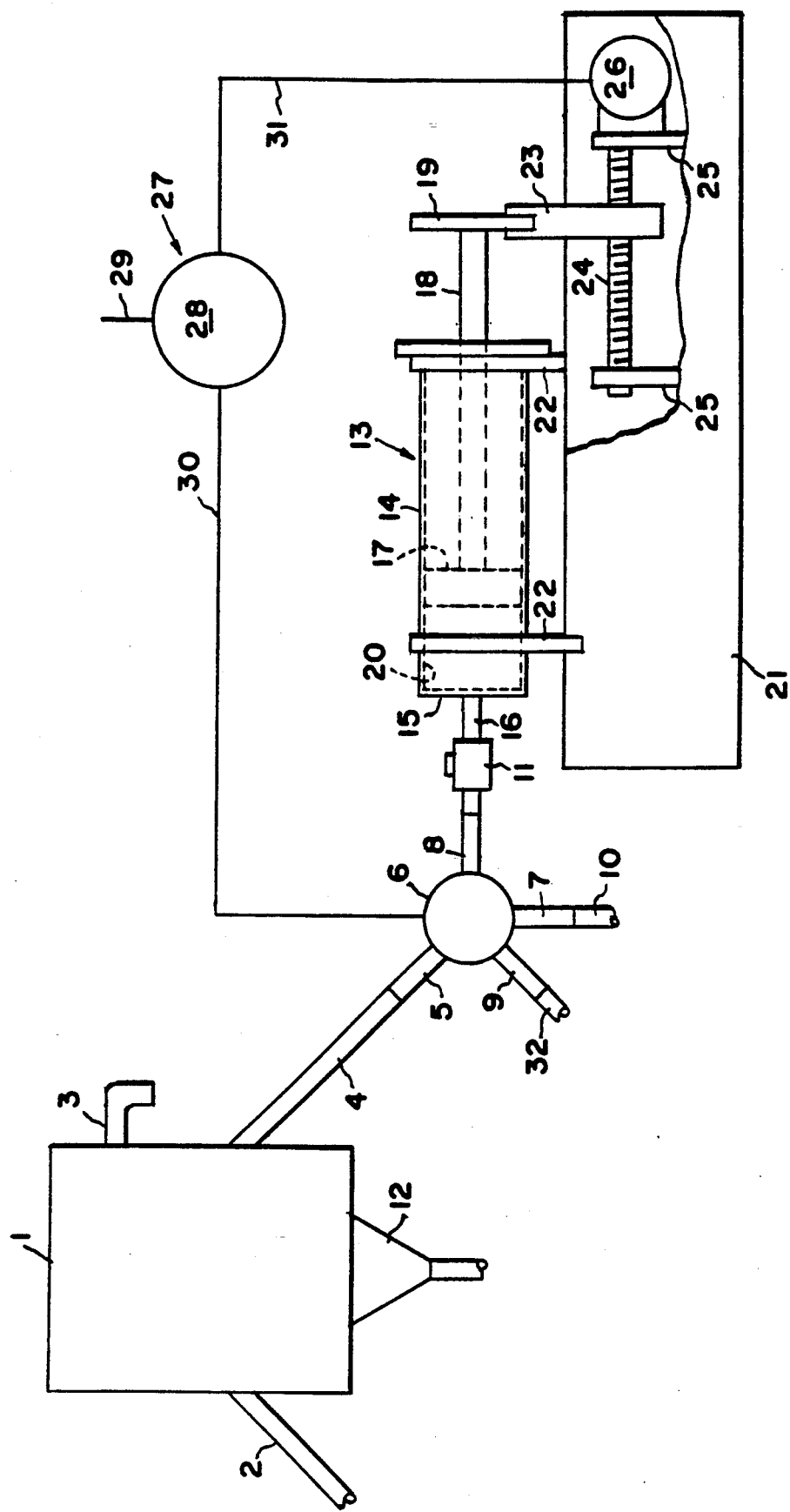

PERIODICALLY ACTIVATED CONSTANT PRESSURE MAINTAINING PISTONED CHAMBER LIQUID SAMPLER

RELATED APPLICATION

This application is a continuation in part of application Ser. No. 07/316,274 filed Feb. 27, 1989, now abandoned.

BACKGROUND OF THE INVENTION

Sampling of liquids containing volatile organic compounds conventionally is accomplished by periodically filling a container formed of glass or other inert material to overflowing and capping the container with an inert closure in such manner as to ensure the absence of any head space, thereby precluding absorption or desorption of any volatile organic compounds which may be present in the liquid. The samples thus obtained may be stored for a short period of time and transported to a laboratory wherein each sample is analyzed in a conventional manner. This procedure is known as the grab sample system.

Although the periodic collection of multiple samples using the grab sample system makes possible the analysis of the liquid as it was constituted at the time each grab sample was taken, the composition of a monitored stream or reservoir may vary considerably between the taking of successive grab samples. Thus, periodically extracted grab samples cannot produce truly representative samples of the content of the stream or reservoir over any appreciable period of time.

One way in which inconsistencies resulting from the periodic taking of grab samples may be minimized is to monitor the stream or reservoir continuously. However, continuous monitoring not only can provide too much data, but it is extremely costly in terms of time, manpower, and equipment.

It previously has been proposed to collect a plurality of individual samples in a single container over a period of time so as to obtain in the same container a plurality of samples that are more representative of the contents of a stream or reservoir. Such proposals, however, have caused the samples to be subjected to periodic changes in pressure, thereby establishing conditions which could lead to inaccuracies in the analysis of such samples, particularly in those instances in which the samples contain volatile compounds.

Sampling methods and apparatus according to the invention overcome the inadequacies and objectionable characteristics of prior art equipment and techniques by introducing to a single gas tight container a plurality of individual samples of precise volume extracted periodically over a selected period of time and without subjecting either the individual or collected samples to pressure changes, thereby enabling the contents of the single container to comprise a representative composite of the contents of the stream or reservoir over such period of time.

SUMMARY OF THE INVENTION

Apparatus for taking a plurality of samples from a stream or reservoir utilizes a sample container having a hollow body and a displaceable piston the position of which defines a variable volume chamber within the container for the accommodation of the samples. The chamber is coupled via a valve to a source of the liquid that is to be sampled. Periodically the valve is actuated to provide communication between the source and the chamber of the container and the piston is driven a short distance in a direction to expand the volume of the chamber, thereby allowing a corresponding volume of the liquid to be admitted to the chamber. The driving of the piston is at such rate as to cause the volume of the chamber to expand at the same rate that a corresponding volume of liquid is admitted to the chamber, thereby avoiding subjecting the liquid to any pressure changes. Following the admission of the liquid sample to the sample chamber, the movement of the piston is discontinued and the valve is actuated to isolate the sample container from the liquid source.

The operations described above are repeated at successive intervals over a selected period of time so as to admit to the sample chamber a number of samples each of which is representative of the constituency of the liquid source at the time the sample was extracted from such source. Accordingly, the contents, of the sampler chamber comprise a true composite of the liquid stream or reservoir over the period of time that the individual samples were taken.

The materials of the apparatus which contact the sample are non-absorbing, non-adsorbent, non-reactive, non-corrosive, and non-contaminating with to the sample.

The number of samples taken over a period o time, and the size of each sample, may be varied virtually at will within wide limits..

THE DRAWING

The drawing is a diagrammatic illustration apparatus constructed and operable in accordance with the invention.

THE PREFERRED EMBODIMENT

Apparatus constructed in accordance with a presently preferred embodiment of the invention is adapted for use in conjunction with a bubble trap 1 to which liquid is delivered by means of a pump (not shown) or in any other suitable manner via an inlet 2. The trap 1 has an overflow tube 3 which may be coupled to an overflow collector. The bubble trap also has an effluent tube 4 through which bubble-free fluid may flow from the bubble trap 1 to an inlet 5 forming part of a known, electrically operated multi-port valve 6 having three outlet spigots 7, 8, and 9. The valve 6 may be one manufactured and sold by Valco Instruments Co., Inc., Houston, Texas. The outlet spigot 7 is coupled by a tube 10 to a drain or other receiver, whereas the outlet spigot 8 may be coupled to one end of a known, manually adjustable, on-off valve 11. A particle trap 12 is fitted to the bottom of the bubble trap 1 for collecting and disposing of solid particulate material.

The apparatus includes a sample contained 13 having a hollow body 14 formed of glass or other suitable material and provided with a wall 15 at one end that is equipped with a nipple 16 adapted for removable insertion in the valve 11. An acceptable container may comprise a syringe such as that manufactured and sold by Spectrum Medical Industries, Los Angeles, Calif., under catalogue designation No. 185213 or 185214. The container also includes a piston 17 accommodated in the body 14 and forming a flexible, fluid-tight, adjustable seal with the cylindrical wall of the body. To the piston is joined one end of a piston rod 18 fitted with a flange 19 at its free end.

In one position of adjustment of the piston 17 it abuts the inner surface of the end wall 15 and forms a fluid-tight seal therewith. Movement of the piston in a direction away from the wall 15 forms a variable volume chamber 20 for the accommodation of a sample, as will be explained more fully hereinafter.

The container 13 is removably secured to a support 21 by means of known, separable clamps 22. The support may comprise a conventional syringe pump such as that designated model No. 980324 by Harvard Apparatus, South Natick, Mass. Such a pump includes a driven actuator 23 coupled to the flange 19 of the piston rod 18 and threadly mounted on a threaded shaft 24 journalled in supports 25 and fitted to a reversible, electric motor 26.

Apparatus for controlling the operation of the sampler is designated by the reference character 27 and comprises an adjustable timer 28 connected to a source of electrical energy via a cable 29 and to the valve 6 and the motor 26 via cables 30 and 31, respectively. The timer may comprise any one of a number of commercially available units, such as a CHRONTROL model CD-04 timer manufactured by Lindburg Enterprises, Inc., San Diego, Calif.

To condition the apparatus for operation the bubble trap 1 is supplied via the inlet 2 from a source of the liquid to be analyzed. A substantially continuous stream of bubble-free liquid thus may flow through the tube 4 and the inlet 5 to the valve 6. Preferably the bubble trap 1 is located in an elevated position relative to the valve 6 so that the stream of liquid will flow by gravity to the valve at which the liquid is under a static or constant head of pressure.

Normally, the valve 6 is in a position in which fluid delivered to the valve flows to and through the spigot 7 and the tube 10 to a drain or other area.

The nipple 16 of the container 13 is fitted to the valve 11 and the latter opened so as to establish communication between the nipple and the valve spigot 8. At the commencement of sampling operations, the piston 17 will abut the inner surface of the body wall 15 so that the volume of the chamber 20 is virtually zero and no liquid can enter the container via the nipple 16.

At a selected time, as determined by the setting of the adjustable timer 28, a pulse will be transmitted to the valve 6 to close the spigot 7 and open the spigot 8, thereby diverting the stream of liquid from the line 10 to the spigot 8 and thence to the container 13.

Shortly after the establishment of communication between the spigot 8 and the liquid source, the timer 28 will energize the motor 26 to cause the actuator 23 to be driven in a direction to withdraw the piston 17 a short distance from the end wall 15 of the body, thereby expanding the volume of the chamber 20 a selected amount and enabling a corresponding volume of liquid to be admitted to the chamber. The rate of admission of the liquid to the chamber corresponds to the rate of expansion of the chamber, thereby maintaining substantially constant the pressure of-the liquid as it is admitted to the chamber and after it has been accommodated therein.

Following the movement of the piston a predetermined distance to expand the chamber, the timer 28 will deenergize the motor 26. At this point the spigot 8 still will be in communication with the fluid in the line 4. As a consequence, the static head caused by the elevated position of the bubble trap 1 positively will preclude any outflow or leakage of liquid from the chamber 20 toward the valve 6.

Shortly after the deenergization of the motor 26, the timer will actuate the valve 6 to reestablish communication between the liquid source and the discharge line 10, whereupon liquid from the source will be diverted from the sampler.

The foregoing procedure is repeated at periodic intervals, as determined by the setting of the timer 28, so as to enable a plurality of equal volume samples to be admitted in successive increments to the container 13 over a selected period of time. At the conclusion of the selected time period, the body 14 will contain a plurality of uniform samples extracted at uniform time intervals from the liquid flowing from the bubble trap 1 or other source. The contents of the container, therefore, will comprise a composite of the constituency of the liquid over the entire time period during which the samples were extracted and the pressure of the liquid in the container will correspond to that of the liquid at the valve 6.

Upon the expiration of the selected time period, the valve 11 may be closed, following which the container 13 may be unclamped from the support 21, uncoupled from the spigot 8, stored for a period of time if necessary, and taken to laboratory for analysis. As long as the piston 17 remains in fixed position, the chamber 20 will be filled completely with the composite sample, thereby avoiding the presence of any head space or clearance into which volatile organic compounds may escape from the liquid.

All of the materials from which the various parts of the apparatus are made are selected so that those which contact the liquid are inert insofar as the sample is concerned and can neither absorb nor desorb volatile compounds. As a consequence, the liquid may be delivered to and stored within the container without any adverse effects.

The analysis performed on the composite sample in the container 13 may correspond to that performed on samples obtained by the grab method referred to earlier.

If it is desired to discharge the contents of the container 13 to another, portable sample holder, the valve 6 may be adjusted to a position in which the chamber 20 communicates with the spigot 9 and an attached line 32 that communicates with a container (not shown) having physical attributes corresponding to those of the container 13. The motor 26 then may be driven in a direction to cause movement of the piston 17 toward the container wall 15 at such speed that the rate of contraction of the chamber 20 corresponds to the volumetric flow of liquid from the chamber, thereby expelling the contents of the chamber 20 via the spigot 9 and the line 32 to the other container, but avoiding changing the pressure of the liquid.

We claim:

1. Apparatus for sampling a liquid comprising container means; means forming a liquid sample chamber within said container means; means for periodically establishing communication between said chamber and a source of said liquid; and means for enlarging the volume of said chamber while the latter is in communication with said source for admitting to said chamber a volume of said liquid corresponding to and concurrently with the enlargement of said chamber and at a rate to maintain substantially constant the pressure of liquid admitted to and accommodated dated in said chamber.

2. Apparatus according to claim 1 wherein said source comprises a flowing stream of said liquid.

3. Apparatus according to claim 1 wherein the means for periodically establishing communication between said chamber and said source comprises adjustable valve means, and means for adjusting said valve means.

4. Apparatus according to claim 3 wherein the means for adjusting said valve means includes timer means.

5. Apparatus according to claim 1 wherein the means for enlarging the volume of said chamber comprises motor means operable to adjust the volume of said chamber independently of said liquid.

6. Apparatus according to claim 5 including means for intermittently driving said motor means.

7. Apparatus according to claim 6 wherein said means for intermittently driving said motor means includes timer means.

8. Apparatus according to claim 1 wherein the means for enlarging the volume of said chamber is operable following the establishment of communication between said chamber and said source.

9. Apparatus according to claim 8 wherein the means for enlarging the volume of said chamber terminates adjustment of said volume while said chamber is in communication with said source.

10. Apparatus according to claim 1 including means for debubbling said liquid prior to its admission to said chamber., 11. Apparatus according to claim 1 wherein said container comprises a hollow body within which is a piston movable in a direction from one end of said body toward its opposite end to enlarge said chamber, and wherein the means for enlarging the volume of said chamber comprises driving means coupled to said piston for moving the latter independently of said liquid.

12. Apparatus according to claim 11 wherein said chamber is in communication with said source via a nipple carried at said one end of said body.

13. Apparatus according to claim 12 wherein the means for periodically establishing communication between said chamber and said source comprises a valve external of said chamber and movable between open and closed positions.

14. Apparatus according to claim 11 wherein said piston is movable in a direction from said opposite end of said body toward said one end for expelling the contents of said chamber.

15. Apparatus according to claim 1 wherein the means for enlarging the volume of said chamber repeatedly increases such volume in successive, spaced increments.

16. Apparatus according to claim 15 wherein each of said increments is uniform.

17. A method of sampling a liquid comprising coupling a source of said liquid to a variable volume chamber in a liquid sample container; periodically expanding the volume of said chamber; and periodically admitting to said chamber from said source and concurrently with the expansion of the volume of said chamber a quantity of said liquid corresponding in volume to that resulting from each periodic expansion of the volume of said chamber while maintaining substantially constant the pressure of liquid admitted to said chamber and the liquid accommodated in said chamber.

18. The method according to claim 17 including establishing communication between said source and said chamber prior to expanding the volume of said chamber.

19. The method according to claim 18 including maintaining on said liquid a substantially constant force sufficient to prevent liquid in said chamber from flowing outwardly thereof when said chamber is in communication with said source.

20. The method according to claim 18 including discontinuing the expansion of said chamber while said chamber is in communication with said source.

21. The method according to claim 17 including debubbling said liquid prior to admitting said liquid to said chamber.

22. The method according to claim 17 wherein said source comprises a flowing stream of said liquid.

23. The method according to claim 17 wherein said source comprises a flowing stream of said liquid, and wherein between successive admissions of liquid to said chamber said stream is diverted to enable said stream to flow past said container.

24. The method according to claim 17 including expelling the contents of said chamber to another container following the admission of a selected volume of said liquid to said chamber while maintaining substantially constant the pressure of said liquid.

25. The method according to claim 17 wherein said liquid contains at least one volatile organic compound.

26. Apparatus for sampling a liquid comprising container means; means forming a liquid sample chamber within said container means; means for periodically establishing communication between said chamber and a source of said liquid under pressure; and means for enlarging the volume of said chamber independently of said liquid and while said chamber is in communication with said source for admitting to said chamber a volume of said liquid corresponding to the enlargement of said chamber and at a rate corresponding to the rate of enlargement of said chamber, thereby maintaining substantially constant the pressure of liquid admitted to said chamber and the pressure of liquid accommodated in said chamber.

27. A method of sampling a liquid comprising coupling a source of said liquid at a predetermined pressure to a variable volume chamber in a liquid sample container; periodically expanding the volume of said chamber independently of said liquid; and periodically admitting to said chamber from said source and in time relation to the expansion of the volume of said chamber a quantity of said liquid corresponding in volume to that resulting from each periodic expansion of the volume of said chamber while maintaining substantially constant the pressure of liquid at said source, the pressure of liquid admitted to said chamber and the pressure of liquid accommodated in said chamber.

* * * * *